(12) United States Patent
Kanemasa (10) Patent No.: US 10,130,794 B2
(45) Date of Patent: Nov. 20, 2018

(54) MEDICAL INSTRUMENT, AND MEDICAL-INSTRUMENT PRODUCTION METHOD

(71) Applicant: SUMITOMO BAKELITE CO., LTD., Tokyo (JP)

(72) Inventor: Kenichi Kanemasa, Akita (JP)

(73) Assignee: SUMITOMO BAKELITE COMPANY LIMITED, Tokyo (JP)

( * ) Notice: Subject to any disclaimer, the term of this patent is extended or adjusted under 35 U.S.C. 154(b) by 641 days.

(21) Appl. No.: 14/417,979

(22) PCT Filed: Jul. 26, 2013

(86) PCT No.: PCT/JP2013/070347
§ 371 (c)(1),
(2) Date: Jan. 28, 2015

(87) PCT Pub. No.: WO2014/021221
PCT Pub. Date: Feb. 6, 2014

(65) Prior Publication Data
US 2015/0202409 A1 Jul. 23, 2015

(30) Foreign Application Priority Data

Aug. 3, 2012 (JP) ................. 2012-173075

(51) Int. Cl.
*A61M 25/01* (2006.01)
*F16C 1/20* (2006.01)
*A61M 25/00* (2006.01)

(52) U.S. Cl.
CPC .... *A61M 25/0147* (2013.01); *A61M 25/0009* (2013.01); *A61M 25/0045* (2013.01); *F16C 1/20* (2013.01); *A61M 2025/0046* (2013.01)

(58) Field of Classification Search
CPC .......... A61M 25/0009; A61M 25/0012; A61M 25/0133; A61M 25/0147;

(Continued)

(56) References Cited

U.S. PATENT DOCUMENTS 5,231,989 A * 8/1993 Middleman ........ A61B 1/00165
600/434
5,308,324 A 5/1994 Hammerslag et al.
(Continued)

FOREIGN PATENT DOCUMENTS

CA 1324553 C 11/1993
JP 57-116924 A 7/1982
(Continued)

OTHER PUBLICATIONS

European Search Report dated Mar. 10, 2016, issued in counterpart European Patent Application No. 13825133.5 (7 pages).
(Continued)

*Primary Examiner* — Andrew Gilbert
*Assistant Examiner* — James D Ponton
(74) *Attorney, Agent, or Firm* — Westerman, Hattori, Daniels & Adrian, LLP (57) ABSTRACT

The present invention relates to a medical instrument capable of enhancing the slidability of an operating wire in a lumen. The medical instrument (for example, a catheter (10) of the present invention) includes: a medical instrument body (a sheath (16)) which has a long length and flexibility and is inserted into a body cavity; a lumen (for example, a sub-lumen (30)) which is formed in the medical instrument body along a longitudinal direction of the medical instrument body; and an operating wire (40). The operating wire (40) is accommodated in the lumen, extends along a longitudinal direction of the lumen, and is slidable in the longitudinal direction of the lumen, and the medical instrument body can be bent by an operation of pulling the operating wire (40). A lubricating liquid (45) adheres to at least a surface of the operating wire (40).

11 Claims, 6 Drawing Sheets

(58) Field of Classification Search
CPC .. A61M 2025/0046; A61M 2025/0062; A61M 2025/015
See application file for complete search history.

(56) References Cited

U.S. PATENT DOCUMENTS

| | | |
|---|---|---|
| 6,497,709 B1 * | 12/2002 | Heath .............. A61B 17/22012 606/127 |
| 2005/0027212 A1 | 2/2005 | Segner et al. |
| 2006/0151923 A1 | 7/2006 | Wilkowske et al. |
| 2011/0009806 A1 | 1/2011 | Melsheimer et al. |
| 2011/0301501 A1 | 12/2011 | Tsunezumi |
| 2013/0304108 A1 * | 11/2013 | Weber .............. A61M 25/0194 606/198 |

FOREIGN PATENT DOCUMENTS

| | | |
|---|---|---|
| JP | 2-180277 A | 7/1990 |
| JP | 2001-043740 A | 2/2001 |
| JP | 2006-192269 A | 7/2006 |
| JP | 2009-515598 A | 4/2009 |
| JP | 2010-207321 A | 9/2010 |
| JP | 2010-227140 A | 10/2010 |
| JP | 2011-251046 A | 12/2011 |
| WO | 2007/059018 A2 | 5/2007 |

OTHER PUBLICATIONS

International Search Report dated Oct. 29, 2013, issued in corresponding application No. PCT/JP2013/070347.
Lu Qingyou et al, "Lubricants for the various sliding blocks and the transmission parts within the endoscopes", Liaoning Science and Technology Press, Apr. 2006, pp. 161, with partial translation.

\* cited by examiner

MEDICAL INSTRUMENT, AND MEDICAL-INSTRUMENT PRODUCTION METHOD

TECHNICAL FIELD

The present invention relates to a medical instrument, and a medical-instrument production method.

Priority is claimed on Japanese Patent Application No. 2012-173075, filed Aug. 3, 2012, the content of which is incorporated herein by reference.

BACKGROUND ART

In PTL 1, a catheter is described which includes a tubular body provided with a lumen (sub-lumen) and an operating wire slidably inserted into the sub-lumen, and is configured such that the tubular body is bent by pulling the operating wire. The operating wire in the literature is a stranded wire formed by stranding a plurality of thin wires together, and in order to enhance the slidability of the operating wire, the surface of the stranded wire is hydrophobized. The hydrophobization is realized by forming a hydrophobic resin layer on the surface of the stranded wire.

CITATION LIST

Patent Literature

[PTL 1] Japanese Unexamined Patent Application, First Publication No. 2010-207321

SUMMARY OF INVENTION

Technical Problem

An object of the present invention is to provide a medical instrument such as a catheter, which is capable of enhancing the slidability of an operating wire in a lumen as in the technique of PTL 1, and a production method for the same.

Solution to Problem

The present invention provides a medical instrument including: a medical instrument body which has a long length and flexibility and is inserted into a body cavity; a lumen which is formed in the medical instrument body along a longitudinal direction of the medical instrument body; an operating wire which is accommodated in the lumen, extends along a longitudinal direction of the lumen, and is slidable in the longitudinal direction of the lumen, the operating wire allowing the medical instrument body to be bent by an operation of pulling the operating wire; and a lubricating liquid which adheres to at least a surface of the operating wire.

According to the medical instrument, since the lubricating liquid adheres to the surface of the operating wire, the sliding resistance of the operating wire against the peripheral wall of the lumen can be reduced, and thus the slidability of the operating wire in the lumen can be enhanced.

In such a case, the lubricating liquid is in a liquid phase and is thus movable in the longitudinal direction of the operating wire. Therefore, even in a case where a point in which the amount of the lubricating liquid in the longitudinal direction of the operating wire is locally insufficient temporarily occurs, the lubricating liquid is smoothly supplied thereto from the other points. Accordingly, local insufficiency of the lubricating liquid in the longitudinal direction of the operating wire can be suppressed.

In addition, the present invention also provides a medical-instrument production method including: an operating wire disposal process of disposing, inside a lumen which is formed in a long medical instrument body along a longitudinal direction of the medical instrument body, an operating wire which extends along a longitudinal direction of the lumen and is slidable in the longitudinal direction of the lumen, and fixing a leading end portion of the operating wire to a leading end portion of the medical instrument body so as to allow the medical instrument body to be in a state of being bent by an operation of pulling the operating wire; and a process of allowing the lubricating liquid to adhere to at least a surface of the operating wire.

Advantageous Effects of Invention

According to the present invention, the slidability of an operating wire within a lumen of a medical instrument can be enhanced.

DESCRIPTION OF EMBODIMENTS

Hereinafter, an embodiment of the present invention will be described with reference to the drawings. In addition, in all of the drawings, like elements are denoted by same reference numerals, and redundant descriptions will be appropriately omitted.

Figure 1:
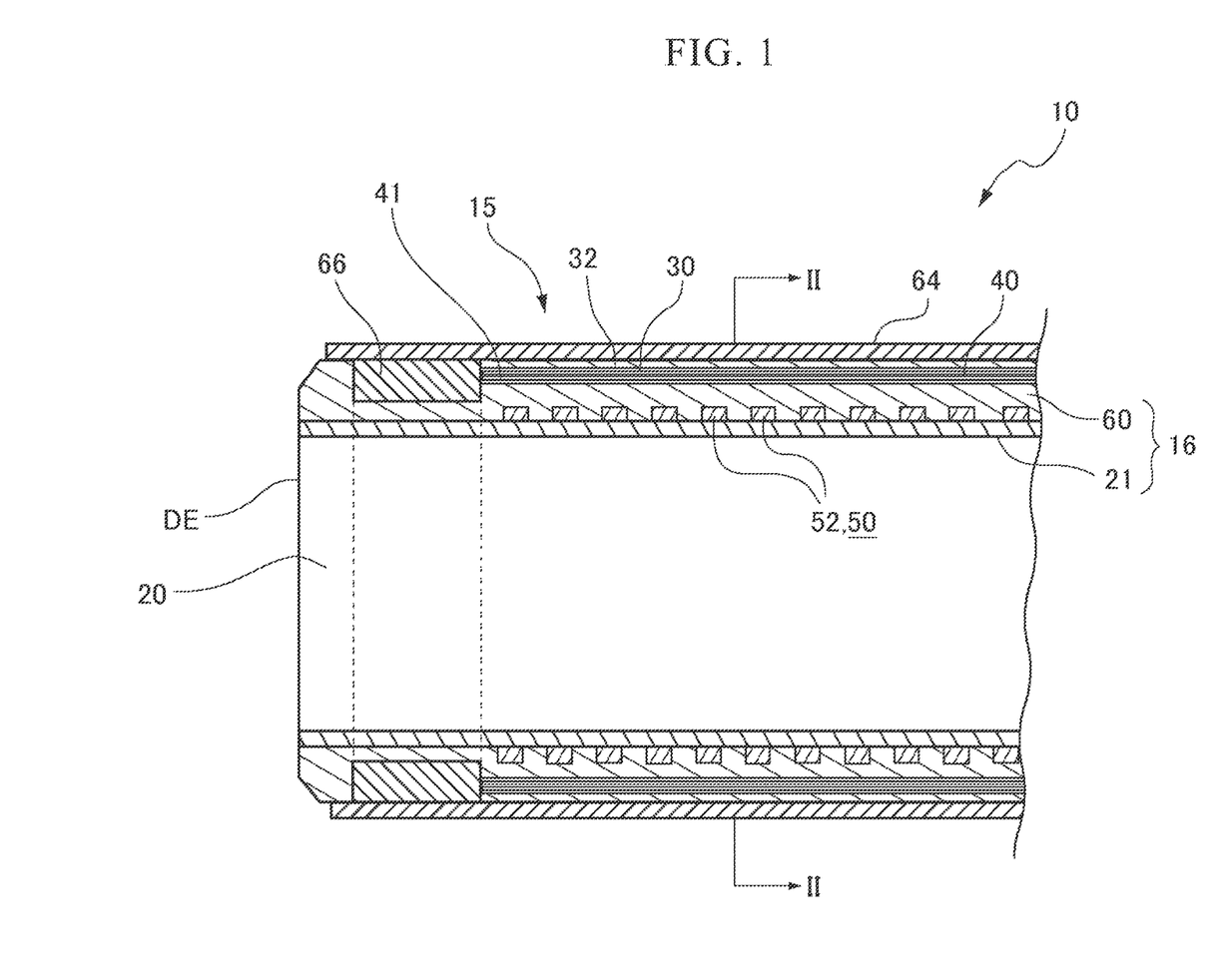
FIG. 1 is a schematic longitudinal sectional view illustrating an example of a catheter as a medical instrument according to an embodiment.
Figure 2:
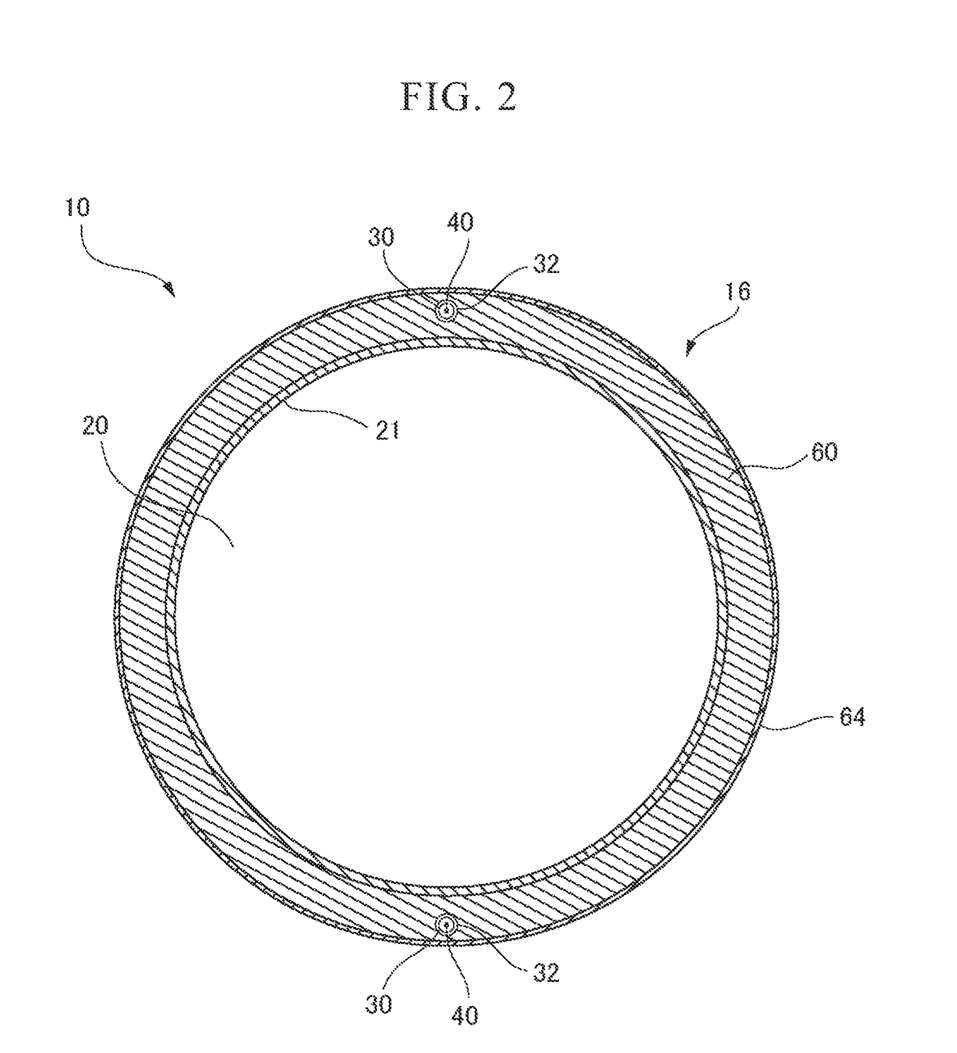
FIG. 2 is a cross-sectional view taken along line II-II of FIG. 1.
Figure 3:
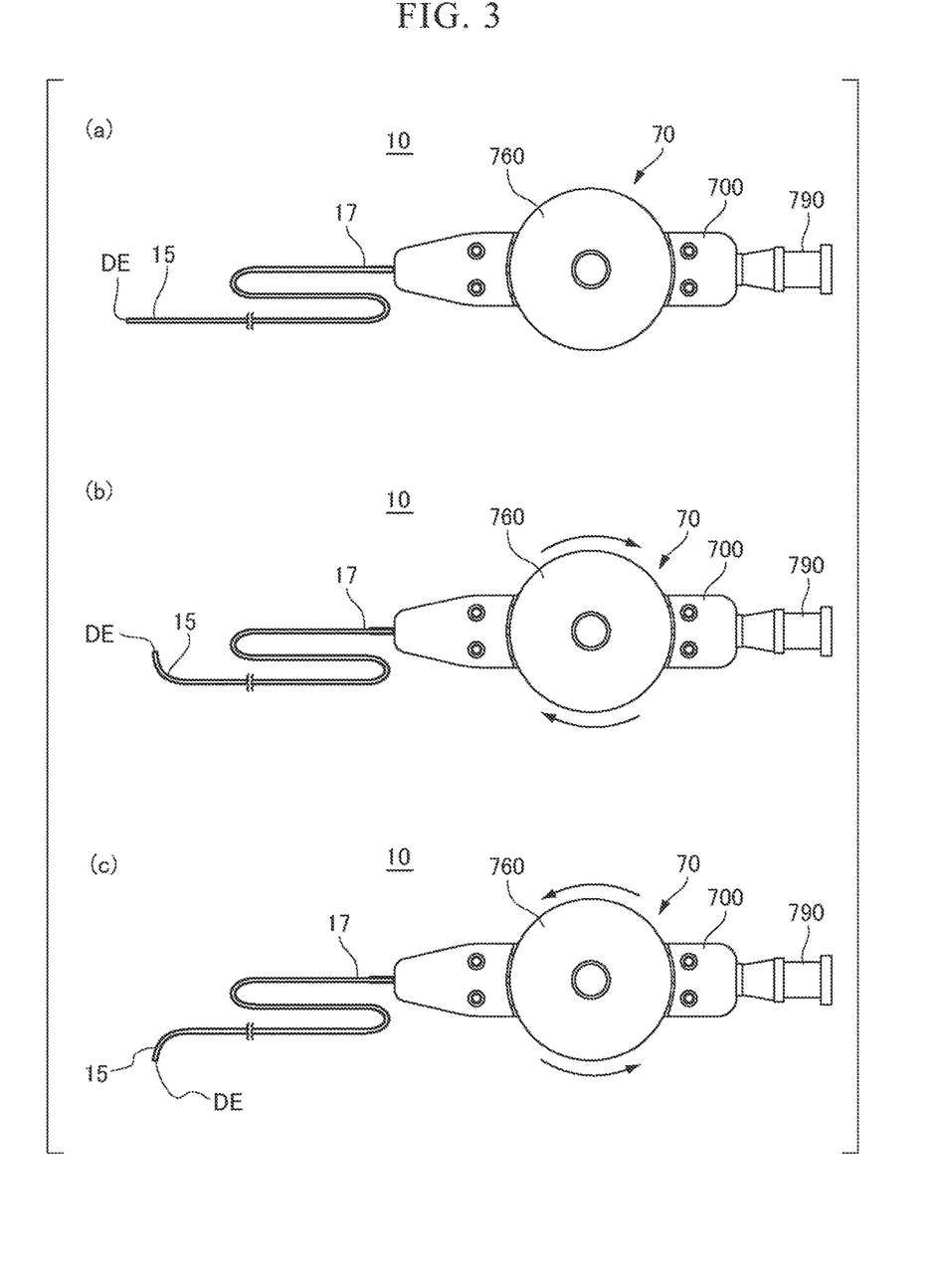
FIG. 3 is a schematic plane view of the catheter according to the embodiment.
Figure 4:
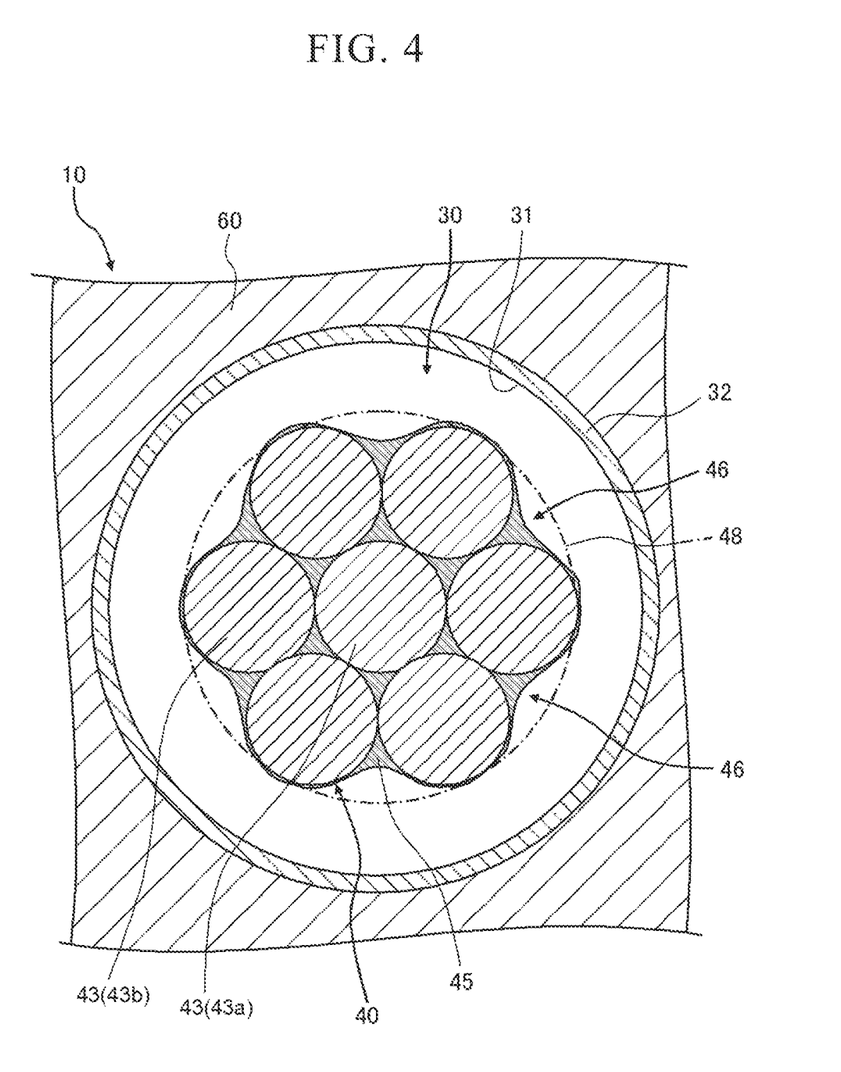
FIG. 4 is a schematic transverse sectional view of the vicinity of a sub-lumen (lumen) of the catheter according to the embodiment.

FIG. 1 is a schematic longitudinal sectional view illustrating the leading end portion of a catheter 10 as a medical instrument according to an embodiment. FIG. 2 is a cross-sectional view taken along line II-II of FIG. 1. FIG. 3 is a schematic plane view of the catheter 10. FIG. 4 is a schematic transverse sectional view of the vicinity of a sub-lumen (lumen) 30 of the catheter 10.

The catheter 10 as the medical instrument according to this embodiment includes a sheath (medical instrument body) 16, a sub-lumen (lumen) 30, an operating wire 40 which is inserted into the sub-lumen 30, and a lubricating liquid 45 (FIG. 4) that adheres to at least the surface of the operating wire 40.

Since the lubricating liquid 45 adheres to the surface of the operating wire 40, the operating wire 40 in the sub-lumen 30 can be provided with good slidability.

The lubricating liquid 45 is not particularly limited as long as it is a liquid having a lubricating action, and may employ a liquid containing a general liquid lubricant, or a liquid obtained by liquefying a general semisolid lubricant such as grease or wax. Examples of the lubricant that can be used as the lubricating liquid 45 include a liquid lubricant such as silicone oil or fluorine oil, and a semisolid lubricant such as silicone grease, fluorine grease, silicone wax, or paraffin wax. Among these, it is preferable to use silicone oil, silicone wax, or silicone grease as the lubricating liquid 45.

In addition, the lubricating liquid mentioned in this specification also includes a fluid obtained by liquefying (fluidifying) a semisolid lubricant such as silicone wax or silicone grease. The liquefying method is not particularly limited, and a typical method such as pressurization or heating may be used.

In addition, the lubricating liquid 45 may also contain, in addition to the lubricant having the lubricating action, other components. The other components include water, a solvent, a dispersant, and the like.

The sheath 16 is the body of the catheter 10. The sheath 16 has a long length and flexibility and is inserted into a body cavity.

In addition, in this specification, a predetermined length region including the distal end (leading end) DE (FIGS. 1 and 3) of the catheter 10 (and the sheath 16) is referred to as a distal end portion 15 of the catheter 10 (and the sheath 16). In the same manner, a predetermined length region including the proximal end (base end) (not illustrated) of the catheter 10 (and the sheath 16) is referred to as a proximal end portion (base end portion) 17 (FIG. 3) of the catheter 10 (and the sheath 16).

An appropriate example of the catheter 10 is an intracatheter which is used by inserting the sheath 16 into a blood vessel. More specifically, as an appropriate example, the sheath 16 is formed to have dimensions such that the sheath 16 can enter any of the eight segments of the liver.

As illustrated in FIGS. 1 and 2, inside the sheath 16, a main lumen 20 and the sub-lumen 30 are formed. Each of the main lumen 20 and the sub-lumen 30 extends along the longitudinal direction (the horizontal direction of FIG. 1) of the sheath 16 (of the catheter 10).

The catheter 10 includes, for example, a plurality of sub-lumens 30.

Each of the sub-lumens 30 has a smaller diameter than that of the main lumen 20. In other words, the main lumen 20 having a greater diameter than that of the sub-lumen 30 is formed in the sheath 16 along the longitudinal direction of the sheath 16.

As illustrated in FIG. 2, in the transverse cross-section of the sheath 16, the sub-lumens 30 and the main lumen 20 are individually disposed so that the sub-lumens 30 are separated from each other and the sub-lumens 30 and the main lumen 20 are separated from each other.

The main lumen 20 is disposed, for example, at the center of the transverse cross-section (a cross-section perpendicular to the longitudinal direction) of the sheath 16.

A plurality of the sub-lumens 30 are, for example, disposed to be dispersed in the periphery of the main lumen 20. In the case of this embodiment, for example, the number of sub-lumens 30 is two, and the sub-lumens 30 are disposed in the periphery of the main lumen 20 at an interval of 180 degrees.

The operating wire 40 is inserted into each of the sub-lumens 30. In the case of this embodiment, the catheter 10 includes, for example, two operating wires 40.

The operating wire 40 is accommodated in the sub-lumen 30 and extends along the longitudinal direction of the sub-lumen 30. That is, the operating wire 40 is buried in the sheath 16 along the longitudinal direction of the sheath 16.

The operating wire 40 slides on the peripheral wall of the sub-lumen 30 and is thus movable in the longitudinal direction of the sub-lumen 30 relative to the sub-lumen 30. That is, the operating wire 40 is slidable in the longitudinal direction of the sub-lumen 30.

As illustrated in FIG. 4, in the case of this embodiment, the operating wire 40 is a stranded wire formed by stranding a plurality of thin wires 43 together.

More specifically, for example, the plurality of thin wires 43 forming the operating wire 40 include a first thin wire 43a disposed at the center of the transverse cross-section of the operating wire 40, and a plurality of second thin wires 43b disposed in the periphery of the first thin wire 43a in the transverse cross-section of the operating wire 40. The number of first thin wires 43a is, for example, one. The second thin wires 43b are wound around the periphery of the first thin wire 43a in a spiral shape.

For example, in the transverse cross-section of the operating wire 40, the second thin wires 43b which are adjacent to each other come into contact with each other, and each of the second thin wires 43b comes into contact with the first thin wire 43a.

For example, the plurality of second thin wires 43b are arranged on the circumference centered at the first thin wire 43a at equal intervals in the transverse cross-section of the operating wire 40.

In the case of this embodiment, more specifically, the operating wire 40 is formed by stranding seven thin wires 43 having the same diameter together. The single thin wire 43 disposed at the center among the seven thin wires 43 is the first thin wire 43a, and the other six thin wires 43 (the second thin wires 43b) are uniformly arranged on the periphery of the first thin wire 43a. That is, as illustrated in FIG. 4, in the transverse cross-section of the operating wire 40, the seven thin wires 43 are arranged in a honeycomb shape so as to have point symmetry.

In addition, the tensile moduli of the thin wires 43 forming the operating wire 40 in the longitudinal direction thereof may be equal to each other but may also be different from each other (details will be described later).

As illustrated in FIG. 4, the lubricating liquid 45 is, for example, not only adhered to the surface of the operating wire 40 but also present in the gap between the adjacent thin wires 43. That is, for example, a portion of the lubricating liquid 45 is held in the gap between the adjacent thin wires 43.

A case where the lubricating liquid 45 on the surface of the operating wire 40 is adhered to the inner peripheral surface of a hollow tube 32, that is, the peripheral wall 31 of the sub-lumen 30, by pulling the operating wire 40 and a phenomenon in which the lubricating liquid 45 on the surface of the operating wire 40 is locally insufficient may be considered. However, the lubricating liquid 45 in the gap between the thin wires 43 oozes to the surface of the operating wire 40 and thus the amount of the lubricating liquid 45 on the surface of the operating wire 40 is appropriately maintained. Therefore, the slidability of the operating wire 40 in the sub-lumen 30 is maintained.

In addition, in a case where there are points where the amount of the lubricating liquid 45 is locally excessive in the longitudinal direction of the sub-lumen 30, the extra lubricating liquid 45 is absorbed by the gap between the adjacent thin wires 43 as the operating wire 40 is caused to slide in the longitudinal direction of the sub-lumen 30 by an operation, and thus the phenomenon in which the amount of the lubricating liquid 45 is locally excessive can be solved.

The amount of the lubricating liquid 45 being adhered to the operating wire 40 is arbitrary. However, when the amount of the lubricating liquid 45 is excessive, there is a possibility that the lubricating liquid 45 may overflow from the opening of the base end side of the sub-lumen 30 due to the pulling operation.

As described later in detail, in the production process of the catheter 10, the operating wire 40 to which the lubricating liquid 45 is adhered is drawn into the sub-lumen 30 from the opening formed at one end of the hollow tube 32 such that the operating wire 40 is disposed inside the sub-lumen 30. When the amount of the lubricating liquid 45 is excessive, during this operation, the lubricating liquid 45 is peeled off from the operating wire 40 by the hollow tube 32 at one end of the hollow tube 32 and thus the lubricating liquid 45 overflows therefrom.

In this embodiment, as illustrated in FIG. 4, in the transverse cross-section of the operating wire 40, the amount of the lubricating liquid 45 is adjusted such that the lubricating liquid 45 is present inside a virtual circle which circumscribes the operating wire 40 (hereinafter, simply referred to as circumscribed circle 48) at an intermediate portion 46 between the adjacent thin wires 43. In other words, in the intermediate portion 46, the amount of the lubricating liquid 45 is adjusted such that the lubricating liquid 45 does not leak out of the circumscribed circle 48. Therefore, the amount of the lubricating liquid 45 does not become excessive, and the occurrence of the above-described problems can be suppressed.

As the material of the thin wires 43 forming the stranded wire, in addition to a flexible metal wire such as low carbon steel (piano wire), stainless steel (SUS), titanium, and titanium alloy, a polymer fiber such as poly(para-phenylene benzobisoxazole) (PBO), polyether ether ketone (PEEK), polyphenylene sulfide (PPS), polybutylene terephthalate (PBT), polyimide (PI), polytetrafluoroethylene (PTFE), and boron fiber may be used.

The outer diameter of the operating wire 40 (the diameter of the circumscribed circle 48 of the stranded wire) may be, for example, 25 to 55 μm.

Through an operation of pulling the operating wire 40, the sheath 16 can be bent in a direction intersecting the axial direction of the sheath 16.

As the structure of the sub-lumen 30, for example, the following two structures may be exemplified.

In a first structure, as illustrated in FIGS. 1, 2, and 4, the hollow tube 32 formed in advance is buried in an outer layer 60 (described later) along the longitudinal direction of the sheath 16, and the inner cavity of the hollow tube 32 functions as the sub-lumen 30. That is, in this structure, the sub-lumen (lumen) 30 is formed by the inner cavity of the hollow tube 32 buried in the sheath 16.

The hollow tube 32 may be formed of, for example, a thermoplastic resin. As the thermoplastic resin, a low-friction resin such as polytetrafluoroethylene (PTFE) or polyether ether ketone (PEEK) may be employed.

In a second structure, the sub-lumen 30 is formed by forming a long hollow portion in the outer layer 60 (described later) along the longitudinal direction of the sheath 16.

More specifically, for example, the sheath 16 includes an inner layer 21, the outer layer 60 formed to be laminated on the periphery of the inner layer 21, and a coating layer 64 formed on the periphery of the outer layer 60.

The inner layer 21 is made of a tubular resin material. The main lumen 20 is formed at the center of the inner layer 21.

The outer layer 60 is made of the same type as or a different type of material from the resin material of the inner layer 21. The sub-lumen 30 is formed inside the outer layer 60.

Examples of the material of the inner layer 21 include a fluorine-based thermoplastic polymer material. Specifically, the fluorine-based thermoplastic polymer material is, for example, polytetrafluoroethylene (PTFE), polyvinylidene difluoride (PVDF), or perfluoroalkoxy fluororesin (PFA).

By making the inner layer 21 of such a fluorine-based resin, delivery properties are enhanced when a contrast medium, a liquid medicine, or the like is supplied to an affected area through the main lumen 20.

Examples of the material of the outer layer 60 include a thermoplastic polymer. As the thermoplastic polymer, polyimide (PI), polyamide-imide (PAI), polyethylene terephthalate (PET), polyethylene (PE), polyamide (PA), nylon elastomer, polyurethane (PU), ethylene-vinyl acetate resin (EVA), polyvinyl chloride (PVC), or polypropylene (PP) may be employed.

The sheath 16 is made of, for example, a resin material. That is, the sheath 16 is configured to include the outer layer 60 and the inner layer 21 which are respectively made of resin materials.

In other words, the sheath 16 includes a hollow resin layer including the outer layer 60 and the inner layer 21.

The resin layer is disposed coaxially with a reinforcing layer 50, which will be described later, and covers the reinforcing layer 50. That is, the reinforcing layer 50 is buried in the resin layer.

The resin material forming the sheath 16 may contain an inorganic filler. For example, as the resin material forming the outer layer 60 which occupies most of the thickness of the sheath 16, a resin material containing an inorganic filler may be used.

Examples of the inorganic filler include barium sulfate and bismuth subcarbonate. By incorporating the inorganic filler into the outer layer 60, X-ray radiopacity is enhanced.

The coating layer 64 forms the outermost layer of the catheter 10 and is made of a hydrophilic material. In addition, the coating layer 64 may be formed in a region of the length of a portion of the distal end portion 15 of the sheath 16 or may also be formed over the entire length of the sheath 16.

The coating layer 64 is molded of, for example, a hydrophilic resin material such as polyvinyl alcohol (PVA) or polyvinylpyrrolidone and does have hydrophilicity. Otherwise, the coating layer 64 may also be formed by performing a lubricating treatment on the outer surface of the outer layer 60 so as to cause at least the outer surface of the outer layer 60 to have hydrophilicity.

For example, the catheter 10 further includes the reinforcing layer 50 having a tubular shape disposed in the periphery of the inner layer 21. As the reinforcing layer 50, for example, a braided layer formed by braiding a plurality of wire rods 52 formed of an elastic body, in a mesh shape may be employed. For example, using metal as the material of the wire rod 52 is a preferable example. However, the material is not limited to this example, and other materials (for example, resins and the like) may also be used as long as the material has a higher rigidity than that of the inner layer 21 or the outer layer 60 and has elasticity. Specifically, as the metal material of the wire rod 52, for example, stainless steel (SUS), a nickel-titanium alloy, steel, titanium, or a copper alloy may be used. The cross-sectional shape of the wire rod 52 is not particularly limited, and for example, is preferably a rectangular shape or a circular shape.

The reinforcing layer 50 is included in the outer layer 60.

The reinforcing layer 50 may also be a coil formed by bending and winding the wire rod 52 in a spiral shape.

In this embodiment, the sub-lumen 30 is formed inside the outer layer 60 on the outside of the reinforcing layer 50.

Representative dimensions of each element of the catheter 10 of this embodiment will be described.

The radius of the main lumen 20 may be about 200 to 300 μm, the thickness of the inner layer 21 may be about 10 to 30 μm, the thickness of the outer layer 60 may be about 50 to 150 μm, the outer diameter of the reinforcing layer 50 may be 500 to 860 μm in diameter, and the inner diameter of the reinforcing layer 50 may be 420 to 660 μm in diameter.

The radius (distance) from the axis of the catheter 10 to the center of the sub-lumen 30 is about 300 to 450 μm, and the inner diameter (diameter) of the sub-lumen 30 is 40 to 100 μm. In addition, the thickness of the operating wire 40 is about 30 to 60 μm.

The outermost diameter (radius) of the catheter 10 is about 350 to 490 μm, that is, the outer diameter thereof is less than 1 mm in diameter. Accordingly, the catheter 10 of this embodiment can be inserted into a blood vessel such as the celiac artery.

A ring-like marker 66 made of a material which does not allow radiation such as X-rays to pass therethrough is provided in the distal end portion 15 of the sheath 16 of the catheter 10. Specifically, the marker 66 is made of a metal material such as platinum. The marker 66 is, for example, provided in the periphery of the main lumen 20 inside the outer layer 60. The marker 66 is, for example, caulked and fixed to the periphery of the inner layer 21 so as to be provided in the distal end portion 15 of the sheath 16.

A leading end portion 41 (FIG. 1) of the operating wire 40 is fixed to the distal end portion 15 of the sheath 16. The form in which the leading end portion 41 of the operating wire 40 is fixed to the distal end portion 15 is not particularly limited. For example, the leading end portion 41 may be welded or fastened to the marker 66, may be fused to the distal end portion 15 of the sheath 16, and may also be adhered and fixed to the marker 66 or the distal end portion 15 of the sheath 16 with an adhesive.

The sub-lumen 30 is open to at least the proximal end side of the catheter 10. The base end portion of each of the operating wires 40 protrudes from the opening of the sub-lumen 30 toward the proximal end side.

As illustrated in FIG. 3, the catheter 10 includes an operating unit 70 provided at the base end portion of the sheath 16. The operating unit 70 forms an operating mechanism for performing an operation of bending the leading end portion of the sheath 16 together with the operating wire 40 (FIGS. 1, 2, and 4).

The operating unit 70 includes, for example, a body case 700, and a wheel-operating unit 760 provided to be rotatable relative to the body case 700.

The base end portion of the sheath 16 is introduced into the body case 700. A hub 790 is attached to the rear end portion of the body case 700. The base end of the sheath 16 is fixed to the front end portion of the hub 790.

The hub 790 is a tubular body having a hollow portion therein which passes through the hub 790 to the forward and rearward directions. The hollow portion of the hub 790 communicates with the main lumen 20 of the sheath 16.

An injector (syringe) (not illustrated) can be inserted into the hub 790 from the rear side thereof. By injecting a liquid such as liquid medicine into the hub 790 using the injector, the liquid can be supplied to the leading end of the sheath 16 via the main lumen 20 and the liquid can be supplied into the body cavity of a patient from the leading end of the sheath 16. That is, the main lumen 20 is open to the distal end DE of the sheath 16 and thus the liquid can be supplied to the distal end from the proximal end of the sheath 16 via the main lumen 20.

For example, the operating wire 40 and the hollow tube 32 branch off from the sheath 16 (a part of the sheath 16 excluding the operating wire 40 and the hollow tube 32) at the front end portion of the body case 700.

The base end portion of the hollow tube 32 is open, and the base end portion of the operating wire 40 protrudes from the opening of the base end portion of the hollow tube 32 toward the proximal end side.

The base end portion of each of the operating wires 40 is directly or indirectly connected to the wheel-operating unit 760. By performing an operation of rotating the wheel-operating unit 760 in any direction, the operating wires 40 can be individually pulled toward the base end side in order to bend the distal end portion 15 of the catheter 10 (the distal end portion 15 of the sheath 16).

As illustrated in FIG. 3(b), when the operation of rotating the wheel-operating unit 760 in one direction around the rotating shaft thereof is performed, one operating wire 40 is pulled toward the base end side. A tensile force is then applied to the distal end portion 15 of the catheter 10 through one operating wire 40. Accordingly, the distal end portion 15 of the sheath 16 is bent toward the side of the sub-lumen 30 into which one operating wire 40 is inserted with respect to the axis of the sheath 16. That is, the distal end portion 15 of the sheath 16 is bent in one direction.

In addition, as illustrated in FIG. 3(c), when the operation of rotating the wheel-operating unit 760 in the other direction around the rotating shaft thereof is performed, the other operating wire 40 is pulled toward the base end side. A tensile force is then applied to the distal end portion 15 of the catheter 10 through the other operating wire 40. Accordingly, the distal end portion 15 of the sheath 16 is bent toward the side of the sub-lumen 30 into which the other operating wire 40 is inserted with respect to the axis of the sheath 16. That is, the distal end portion 15 of the sheath 16 is bent in the other direction.

The bending of the sheath 16 includes a form in which the sheath 16 is bent in an "L" shape and a form in which the sheath 16 is bent in an arc shape.

As described above, the two operating wires 40 are selectively pulled by the operation of the wheel-operating unit 760 of the operating unit 70 and thus the distal end portion 15 of the catheter 10 can be bent in a first direction and a second direction which is the opposite direction. The first direction and the second direction are included in the same plane.

By combining a torque operation of rotating the entire catheter 10 around the axis thereof and the pulling operation, the direction of the distal end DE of the catheter 10 can be controlled.

Furthermore, by controlling the pulling amount of the operating wire 40, the bending amount of the distal end portion 15 of the catheter 10 can be controlled.

Therefore, the catheter 10 of this embodiment can be allowed to enter a body cavity such as a branched blood vessel in a predetermined direction.

That is, by performing the operation of bending the distal end portion 15, a direction in which the catheter 10 enters a body cavity can be changed.

Since the lubricating liquid 45 adheres to the surface of the operating wire 40, when the operating wire 40 is pulled, the surface of the operating wire 40 comes into contact with the peripheral wall 31 (FIG. 4) of the sub-lumen 30, that is, the inner peripheral surface of the hollow tube 32 via the lubricating liquid 45. Therefore, the sliding resistance of the operating wire 40 against the peripheral wall 31 of the sub-lumen 30 can be reduced, and thus the slidability of the operating wire 40 in the sub-lumen 30 can be enhanced.

Next, a medical-instrument production method according to this embodiment will be described.

This production method includes an operating wire disposal process of disposing, inside a lumen (for example, the sub-lumen 30) which is formed in a long medical instrument body (the sheath 16) along the longitudinal direction of the medical instrument body, the operating wire 40 which extends along the longitudinal direction of the lumen and is slidable in the longitudinal direction of the lumen, and fixing the leading end portion 41 of the operating wire 40 to the leading end portion (the distal end portion 15) of the medical instrument body so as to allow the medical instrument body to be in a state of being bent by an operation of pulling the operating wire 40. Furthermore, the production method includes a process of allowing the lubricating liquid 45 to adhere to at least the surface of the operating wire 40.

Hereinafter, this will be described in detail.

For example, as described below, each part of the catheter 10 is individually produced, and the parts are combined, thereby producing the catheter 10.

The outer layer 60 is produced by, for example, extruding a resin material as a molding material with an extruding apparatus (not illustrated). During the extrusion, a core wire (mandrel) is extruded along with the resin material such that the resin material which becomes the outer layer 60 adheres to the periphery of the core wire.

The material for the core wire is not particularly limited, and examples thereof include copper, a copper alloy, alloy steel such as carbon steel and SUS, nickel, and a nickel alloy.

A releasing treatment may be arbitrarily performed on the surface of the core wire. As the releasing treatment, in addition to the application of a fluorine-based or silicone-based release agent, an optical or chemical surface treatment may be performed.

The extrusion is performed such that a long hollow portion is formed along the longitudinal direction at each of the positions of the outer layer 60 where the sub-lumens 30 are to be formed later by burying the hollow tubes 32, for example, by supplying a fluid such as gas to the positions. The inner diameter of the hollow portion is greater than the outer diameter of the hollow tube 32. This is done to facilitate a process of inserting the hollow tube 32 into the hollow portion thereafter.

After the extrusion, the core wire is drawn out, thereby producing the outer layer 60 having a hollow shape. In addition, the wire diameter of the core wire used to mold the outer layer 60 is greater than the outer diameter of the reinforcing layer 50. This is done to facilitate a process of covering the periphery of the reinforcing layer 50 (the inner layer 21) with the outer layer 60 thereafter.

The inner layer 21 is produced by extruding a resin material using a different extruding apparatus (not illustrated) from the extruding apparatus for producing the outer layer 60. During the extrusion, a core wire (a different core wire from that for producing the outer layer 60) is extruded along with the resin material such that the resin material which becomes the inner layer 21 adheres to the periphery of the core wire. The wire diameter of the core wire corresponds to the diameter of the main lumen 20. In addition, the inner layer 21 may also be molded with a dispersion molding apparatus.

The braided layer as the reinforcing layer 50 is formed through a process of winding a plurality of wire rods around the periphery of the inner layer 21 in a state where the core wire remains therein, in a mesh shape.

The hollow tube 32 is produced by extruding a resin material using a different extruding apparatus (not illustrated) from the extruding apparatus for producing the inner layer 21 and from the extruding apparatus for producing the outer layer 60. The extrusion is performed while discharging a fluid such as gas from a discharge tube disposed at the center of an extrusion port (nozzle) of the extruding apparatus, thereby forming a hollow portion at the center of the hollow tube 32.

In addition, a dummy core wire to be inserted into the hollow tube 32 is separately provided, and the dummy core wire is inserted into the hollow tube 32.

After producing the outer layer 60 and forming the reinforcing layer 50 in the periphery of the inner layer 21, the periphery of the reinforcing layer 50 is covered with the outer layer 60. Accordingly, the core wire (used to form the inner layer 21), the inner layer 21, the reinforcing layer 50, and the outer layer 60 are in a state of being concentrically arranged in this order from the center side.

Next, the hollow tube 32 (with the dummy core wire) is inserted into each of the hollow portions of the outer layer 60.

Next, the periphery of the outer layer 60 is covered with a heat-shrinkable tube (not illustrated). Next, by heating, the heat-shrinkable tube is allowed to shrink and the periphery thereof is fastened to the outer layer 60, and the outer layer 60 is melted. In addition, the heating temperature is higher than the melting temperature of the outer layer 60 and is lower than the melting temperature of the inner layer 21. Due to the heating, the outer layer 60 and the inner layer 21 are joined together by fusing. At this time, the resin material forming the outer layer 60 includes the reinforcing layer 50 therein and the reinforcing layer 50 is impregnated with the resin material. In addition, it is preferable that the heating temperature at this time be higher than the melting temperature of the outer layer 60 and lower than the melting temperature of the hollow tube 32. Accordingly, the outer layer 60 and the hollow tube 32 are joined together by fusing.

Next, the heat-shrinkable tube is torn by making an incision in the heat-shrinkable tube and the heat-shrinkable tube is removed from the outer layer 60.

In addition, the operating wire 40 is prepared, and the lubricating liquid 45 is allowed to adhere to the operating wire 40 (details are described later).

Next, the dummy core wire is drawn out from the hollow tube 32, and the operating wire 40 is inserted into the hollow tube 32.

That is, the process of allowing the lubricating liquid 45 to adhere to at least the surface of the operating wire 40 is performed before the operating wire disposal process.

When the operating wire 40 is inserted into the hollow tube 32, the operating wire 40 is drawn into the hollow tube 32 from the opening of one end of the hollow tube 32.

That is, in the operating wire disposal process, the operating wire 40 is disposed inside the sub-lumen 30 by drawing the operating wire 40 into the sub-lumen 30 from the opening that is formed at one end of the sub-lumen 30.

In addition, the marker 66, which is an annular metal member, is separately prepared.

Next, fixing of the leading end portion of the operating wire 40 to the marker 66 and caulking and fixing of the marker 66 to the periphery of the leading end portion of the sheath 16 are performed.

Next, the hub 790 is connected to the base end portion of the sheath 16.

Next, the core wire in the inner layer 21 is drawn out. The drawing of the core wire is performed in a state where the core wire is reduced in diameter by pulling both ends of the core wire in the longitudinal direction thereof. Accordingly, a hollow portion which becomes the main lumen 20 is formed at the center of the inner layer 21.

Next, the base end portion of the operating wire 40 is directly or indirectly connected to the wheel-operating unit 760 of the operating unit 70 which is separately produced. Furthermore, the body case 700 and the wheel-operating unit 760 of the operating unit 70 are assembled to each other, and the hub 790 is attached to the body case 700.

In this manner, the sheath 16 is in a state of being bent by the operation of pulling the operating wire 40.

Next, the coating layer 64 is formed. For example, a liquid containing the hydrophilic resin material as described above as the material of the coating layer is allowed to adhere to the surface of the outer layer 60, thereby forming the coating layer 64. The adhesion of the liquid to the outer layer 60 may be performed using, for example, a dip-coating method or a spray coating method.

In this manner, the catheter 10 having the structure as illustrated in FIGS. 1 to 4 can be produced.

An example of the process of allowing the lubricating liquid 45 to adhere to the operating wire 40 will be described. For example, the lubricating liquid 45 is allowed to adhere to the operating wire 40 by dipping the operating wire 40 into a liquid obtained by diluting silicone oil with a solvent, or a liquid obtained by emulsifying silicone oil with an aqueous solvent such as water to be dispersed. For example, while the operating wire 40 is received by a receiving apparatus, the operating wire 40 before being received by the receiving apparatus is dipped into the liquid. In this case, by appropriately adjusting the receiving speed of the receiving apparatus and the liquid concentration, the amount of silicone oil being applied to the operating wire 40 can be controlled.

Furthermore, in a case where the lubricating liquid 45 is allowed to adhere to the operating wire 40 by this method, the lubricating liquid 45 that adheres to the operating wire 40 is formed of the silicone oil diluted with the solvent, or the aqueous solvent and the silicone oil emulsified with the aqueous solvent to be dispersed.

Figure 5:
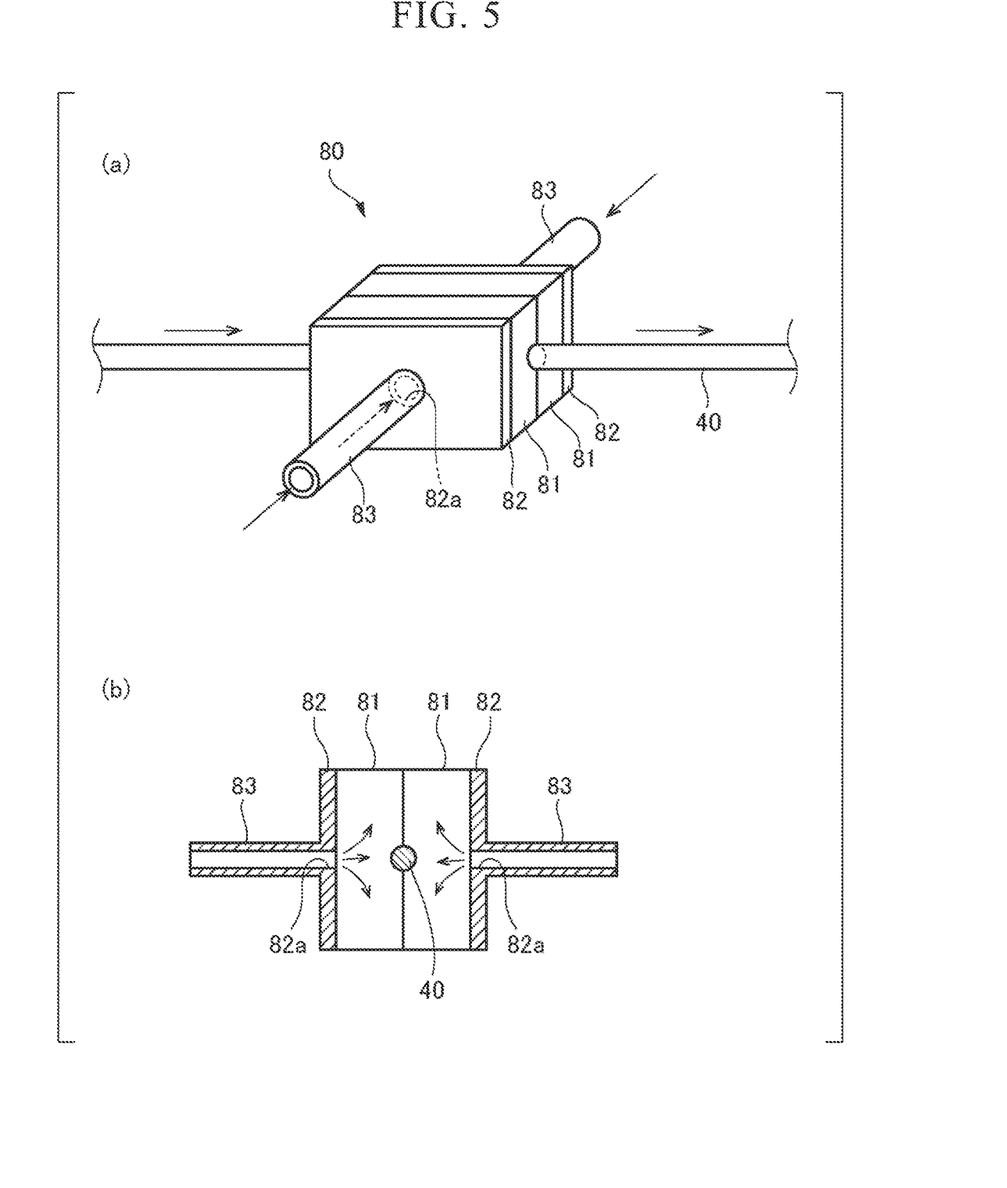
FIG. 5 is a schematic view illustrating a catheter production method according to the embodiment.

Next, another example of the process of allowing the lubricating liquid 45 to adhere to the operating wire 40 will be described with reference to FIG. 5. FIG. 5 is a schematic view illustrating an adhesion mechanism 80 which allows the lubricating liquid 45 to adhere to the operating wire 40, in which FIG. 5(*a*) is a perspective view and FIG. 5(*b*) is a cross-sectional view perpendicular to the longitudinal direction of the operating wire 40.

As illustrated in FIG. 5, the adhesion mechanism 80 includes, for example, an application unit 81 which comes into contact with the operating wire 40 to apply the lubricating liquid 45 to the operating wire 40, a holding unit 82 which holds the application unit 81, and a supply tube 83 which supplies the lubricating liquid 45 to the application unit 81.

The application unit 81 is formed of fiber such as non-woven fabric, which absorbs and holds the lubricating liquid 45. The adhesion mechanism 80 includes, for example, a pair of application units 81 which are disposed to oppose each other. For example, the pair of application units 81 are pressed against each other with a small force.

The holding unit 82 is, for example, supported by a supporting mechanism (not illustrated). For example, the supporting mechanism biases a pair of holding units 82 in a direction in which the pair of holding units 82 approach each other. Accordingly, the pair of application units 81 are pressed against each other.

For example, one end of the supply tube 83 is fixed to the holding unit 82. A part of the holding unit 82 which corresponds to one end of the supply tube 83 is provided with a supply port 82*a*, and the inside of the supply tube 83 and the application unit 81 side communicate with each other via the supply port 82*a*.

The lubricating liquid 45 is supplied to the application unit 81 from a tank (not illustrated) through the supply tube 83 and the supply port 82*a* in this order and is absorbed and held by the application unit 81.

By allowing the operating wire 40 to pass between the pair of application units 81, the lubricating liquid 45 can be allowed to adhere to at least the surface of the operating wire 40.

That is, by allowing fiber (the application unit 81) impregnated with the lubricating liquid 45 to come into contact with the operating wire 40, the process of allowing the lubricating liquid 45 to come into contact with at least the surface of the operating wire 40 is performed.

At this time, while applying the lubricating liquid 45 to the operating wire 40 from the application unit 81, at the same time, an extra amount of the lubricating liquid 45 of the operating wire 40 is wiped off by the application unit 81 so as not to allow the lubricating liquid 45 to excessively adhere to the operating wire 40. Accordingly, an appropriate amount of the lubricating liquid 45, for example, as illustrated in FIG. 4 is allowed to adhere to the operating wire 40. That is, in the transverse cross-section of the operating wire 40, in the intermediate portion 46 between the adjacent thin wires 43, the lubricating liquid 45 can be present inside the circumscribed circle 48 which circumscribes the operating wire 40. In other words, in the intermediate portion 46, the amount of the lubricating liquid 45 can be adjusted such that the lubricating liquid 45 does not leak out of the circumscribed circle 48.

According to the first embodiment as described above, since the lubricating liquid 45 adheres to the surface of the operating wire 40, the sliding resistance of the operating wire 40 against the peripheral wall 31 of the sub-lumen 30 can be reduced, and thus the slidability of the operating wire 40 in the sub-lumen 30 can be enhanced.

The lubricating liquid 45 is in a liquid phase and is thus movable in the longitudinal direction of the operating wire 40. Therefore, even in a case where a point in which the amount of the lubricating liquid 45 in the longitudinal direction of the operating wire 40 is locally insufficient temporarily occurs, the lubricating liquid 45 is smoothly supplied thereto from the other points. Accordingly, local insufficiency of the lubricating liquid 45 in the longitudinal direction of the operating wire 40 can be suppressed.

In addition, typically, it is thought that the lubricating liquid 45 also adheres to the peripheral wall 31 of the sub-lumen 30. Therefore, even in a case where a point in which the amount of the lubricating liquid 45 in the longitudinal direction of the operating wire 40 is locally insufficient temporarily occurs, the point comes into contact with the peripheral wall 31 and the lubricating liquid 45 is supplied to the point from the peripheral wall 31. Even with this operation, local insufficiency of the lubricating liquid 45 in the longitudinal direction of the operating wire 40 can also be suppressed.

In addition, since the operating wire 40 is the stranded wire, a portion of the lubricating liquid 45 is held in the gap between the adjacent thin wires 43. Therefore, even in a case where a phenomenon in which the lubricating liquid 45 on the surface of the operating wire 40 is locally insufficient occurs, the lubricating liquid 45 in the gap between the thin wires 43 oozes to the surface of the operating wire 40 and thus the slidability of the operating wire 40 in the sub-lumen 30 can be maintained.

In addition, the sliding resistance between the thin wires 43 can be reduced through the lubricating liquid 45. Therefore, when the operating wire 40 is bent, the adjacent thin wires 43 can be moved slightly relative to each other in the longitudinal direction of the operating wire 40, and thus the bendability of the operating wire 40, furthermore, the bendability of the catheter 10 can be enhanced.

In addition, the plurality of thin wires 43 forming the operating wire 40 include the first thin wire 43a disposed at the center of the transverse cross-section of the operating wire 40, and the plurality of second thin wires 43b disposed in the periphery of the first thin wire 43a in the transverse cross-section of the operating wire 40. Therefore, the shape of the transverse cross-section of the stranded wire becomes close to a circle, and thus the structure of the operating wire 40 is stabilized.

Particularly, in a case where the operating wire 40 is the stranded wire formed by stranding seven thin wires 43 together, by using the thin wires 43 having the same diameter, the stranded wire in which the adjacent thin wires 43 come into contact with each other as illustrated in FIG. 4 can be formed. In addition, a number of points can hold the lubricating liquid 45 in the gap between the adjacent thin wires 43.

In addition, in the transverse cross-section of the operating wire 40, in the intermediate portion 46 between the adjacent thin wires 43, the lubricating liquid 45 is present inside the circumscribed circle 48 which circumscribes the operating wire 40. Therefore, the overflow of the lubricating liquid 45 from the opening of the base end side of the sub-lumen 30 by the pulling operation can be suppressed. In addition, when the operating wire 40 to which the lubricating liquid 45 adheres is drawn into the hollow tube 32 from one end of the hollow tube 32, removal of the lubricating liquid 45 from the operating wire 40 at one end of the hollow tube 32 can be suppressed.

In this embodiment, the plurality of thin wires 43 forming the operating wire 40 include the first thin wire 43a disposed at the center of the transverse cross-section of the operating wire 40, and the plurality of second thin wires 43b disposed in the periphery of the first thin wire 43a in the transverse cross-section of the operating wire 40. In this case, the path length of the first thin wire 43a is shorter than the path length of the second thin wire 43b per unit of length of the operating wire 40. This is because the first thin wire 43a extends, for example, linearly while the second thin wire 43b is wound around the periphery of the first thin wire 43a in a spiral shape.

Therefore, in a case where the tensile moduli of the first thin wire 43a and the second thin wire 43b in the longitudinal direction thereof are equal to each other, elongation of the second thin wire 43b is relatively easily allowed, while elongation of the first thin wire 43a is less likely to be allowed.

Therefore, it is also preferable to set the tensile modulus of the first thin wire 43a to be lower than the tensile modulus of the second thin wire 43b. That is, the stretchability of the first thin wire 43a which is the thin wire 43 disposed at the center of the operating wire 40 may be increased to be higher than the stretchability of the second thin wire 43b disposed in the periphery of the first thin wire 43a.

Specifically, different materials may be selected for the first thin wire 43a and the second thin wire 43b such that the stretchability of the first thin wire 43a is greater than the stretchability of the second thin wire 43b.

Accordingly, a state in which excessive tension is locally applied to the first thin wire 43a in the longitudinal direction thereof can be suppressed, and thus the tension of the first thin wire 43a can be dispersed and made uniform in the longitudinal direction thereof.

Figure 6:
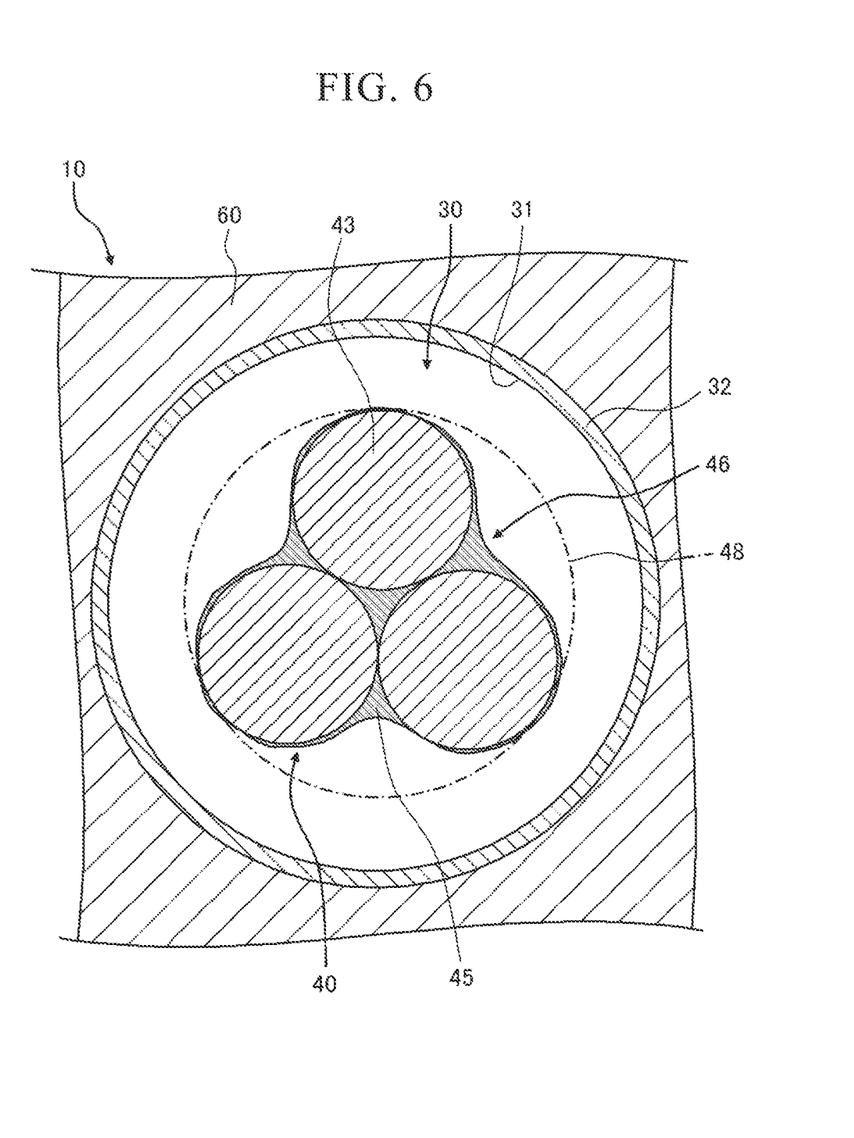
FIG. 6 is a schematic transverse sectional view of the vicinity of the sub-lumen of the catheter according to a modification example.

FIG. 6 is a schematic transverse sectional view of the vicinity of the sub-lumen 30 of the catheter according to a modification example.

In the above description, an example in which the operating wire 40 is formed by stranding the seven thin wires 43 together is described. However, as illustrated in FIG. 6, the operating wire 40 may also be formed by stranding three thin wires 43 together. In this case, for example, the three thin wires 43 are arranged to have point symmetry in the transverse cross-section of the operating wire 40.

In addition, in a case where the operating wire 40 is a stranded wire formed by stranding a plurality of thin wires 43 together, the number of thin wires 43 forming the operating wire 40 may be a number other than three or seven.

Moreover, the operating wire 40 may not be a stranded wire and may also be formed of a single wire rod. Even in this case, the material of the operating wire 40 is the same as the material of the thin wire 43 described above.

In the above description, an example in which the operating wire 40 is inserted into the sub-lumen 30 after the lubricating liquid 45 is allowed to adhere to at least the surface of the operating wire 40 is described. However, the lubricating liquid 45 may also be allowed to adhere to the operating wire 40 by inserting the operating wire 40 into the sub-lumen 30 and thereafter injecting the lubricating liquid 45 into the sub-lumen 30.

Furthermore, a small groove that extends in the longitudinal direction of the operating wire 40 may also be formed on the surface of the operating wire 40. Specifically, for example, in each of the thin wires 43, a small groove that extends in the longitudinal direction thereof may also be formed. In this case, the lubricating liquid 45 can be held in the groove, and thus the slidability of the operating wire 40 can be appropriately maintained.

In the above description, the catheter 10 is exemplified as the medical instrument. However, the present invention is applicable to other medical instruments (for example, an endoscope) in which the slidability of the operating wire 40 needs to be secured.

The elements of each of the above embodiments need not be individually independently present. A plurality of elements may be formed into a single member, a single element may be formed into a plurality of members, a particular element may be a portion of another element, and a portion of a particular element may overlap a portion of another element.

REFERENCE SIGNS LIST 10 catheter
15 distal end portion
16 sheath
17 proximal end portion
20 main lumen 21 inner layer
30 sub-lumen
31 peripheral wall
32 hollow tube
40 operating wire
41 leading end portion
43 thin wire
43a first thin wire
43b second thin wire
45 lubricating liquid
46 intermediate portion
48 circumscribed circle
50 reinforcing layer
52 wire rod
60 outer layer
64 coating layer
66 marker
70 operating unit
80 adhesion mechanism
81 application unit
82 holding unit
82a supply port
83 supply tube
700 body case
760 wheel-operating unit
790 hub
DE distal end

The invention claimed is:

1. A medical instrument comprising:
a medical instrument body which has a length and flexibility such that it is configured to be inserted into a body cavity;
a lumen which is formed in the medical instrument body along a longitudinal direction of the medical instrument body;
an operating wire which is accommodated in the lumen, extends along a longitudinal direction of the lumen, and is slidable in the longitudinal direction of the lumen, the operating wire allowing the medical instrument body to be bent by an operation of pulling the operating wire; and
a lubricating liquid which adheres to at least a surface of the operating wire,
wherein the operating wire is a stranded wire formed by stranding a plurality of thin wires together, and a portion of the lubricating liquid is held in a gap between adjacent thin wires,
wherein the plurality of thin wires comprises a first thin wire disposed at a center of a transverse cross-section of the operating wire, and a plurality of second thin wires disposed in a periphery of the first thin wire in the transverse cross-section of the operating wire,
wherein a small groove that extends in a longitudinal direction of the operating wire is formed on a surface of the first thin wire, and
wherein in the transverse cross-section of the operating wire, in an intermediate portion between the adjacent thin wires, the lubricating liquid is present inside a circumscribed circle which circumscribes the operating wire.

2. The medical instrument according to claim 1, wherein the stranded wire is formed by stranding seven thin wires together.
3. The medical instrument according to claim 1, wherein the stranded wire is formed by stranding three thin wires together.
4. The medical instrument according to claim 1, wherein the lubricating liquid is silicone oil.
5. The medical instrument according to claim 1, wherein the lumen is formed by an inner cavity of a hollow tube which is buried in the medical instrument body.
6. The medical instrument according to claim 1, wherein a main lumen which has a larger diameter than that of the lumen is formed in the medical instrument body along the longitudinal direction of the medical instrument body.
7. The medical instrument according to claim 1, wherein the medical instrument is a catheter.
8. The medical instrument according to claim 1, wherein a tensile modulus of the first thin wire is smaller than a tensile modulus of the plurality of second thin wires.
9. The medical instrument according to claim 1, wherein a small groove that extends in the longitudinal direction of the operating wire is formed on a surface of said plurality of the second thin wires.
10. A medical-instrument production method comprising:
an operating wire disposal process of disposing, inside a lumen which is formed in a medical instrument body along a longitudinal direction of the medical instrument body, an operating wire which extends along a longitudinal direction of the lumen and is slidable in the longitudinal direction of the lumen, and fixing a leading end portion of the operating wire to a leading end portion of the medical instrument body so as to allow the medical instrument body to be in a state of being bent by an operation of pulling the operating wire; and
a process of allowing lubricating liquid to adhere to at least a surface of the operating wire,
wherein in the operating wire disposal process, the operating wire is formed by stranding a first thin wire disposed at a center of a transverse cross-section of the operating wire, and a plurality of second thin wires disposed in a periphery of the first thin wire in the transverse cross-section of the operating wire is used;
wherein a small groove that extends in a longitudinal direction of the operating wire is formed on a surface of the first thin wire, and
wherein in the process of allowing the lubricating liquid to adhere to at least a surface of the operating wire, in the transverse cross-section of the operating wire, in an intermediate portion between the adjacent thin wires, the lubricating liquid is adhered so as to be present inside a circumscribed circle which circumscribes the operating wire.
11. The medical-instrument production method according to claim 10, wherein the process of allowing the lubricating liquid to adhere to at least the surface of the operating wire is performed before the operating wire disposal process.

* * * * *